(12) United States Patent
Hsieh et al.

(10) Patent No.: US 10,502,793 B2
(45) Date of Patent: Dec. 10, 2019

(54) NONLINEAR ACOUSTIC RESONANCE SPECTROSCOPY (NARS) FOR DETERMINING PHYSICAL CONDITIONS OF BATTERIES

(71) Applicant: Feasible, Inc., Emeryville, CA (US)

(72) Inventors: Andrew Gaheem Hsieh, Berkeley, CA (US); Barry James Van Tassell, El Cerrito, CA (US); Robert Charles Mohr, Berkeley, CA (US); Anne Wilkinson, Seattle, WA (US); Jonathan Ajo-Franklin, Berkeley, CA (US); Shaurjo Biswas, El Cerrito, CA (US)

(73) Assignees: THE REGENTS OF THE UNIVERSITY OF CALIFORNIA, Oakland, CA (US); FEASIBLE, INC., Emeryville, CA (US)

( * ) Notice: Subject to any disclaimer, the term of this patent is extended or adjusted under 35 U.S.C. 154(b) by 0 days.

(21) Appl. No.: 15/836,531

(22) Filed: Dec. 8, 2017

(65) Prior Publication Data
US 2018/0164383 A1 Jun. 14, 2018

Related U.S. Application Data

(60) Provisional application No. 62/432,296, filed on Dec. 9, 2016, provisional application No. 62/432,312, filed on Dec. 9, 2016.

(51) Int. Cl.
*G08B 21/00* (2006.01)
*G01R 31/392* (2019.01)
(Continued)

(52) U.S. Cl.
CPC .......... *G01R 31/392* (2019.01); *B60L 3/0046* (2013.01); *B60L 3/12* (2013.01);
(Continued)

(58) Field of Classification Search
CPC ............ G01R 31/3679; G01R 31/3624; G01R 31/3651; G01R 31/3662; H01M 10/486; H01M 2010/4271
(Continued)

(56) References Cited

U.S. PATENT DOCUMENTS

2005/0097961 A1 5/2005 Yagi et al.
2005/0218915 A1 10/2005 Tinnemeyer
(Continued)

OTHER PUBLICATIONS

International Search Report and Written Opinion dated Mar. 1, 2018 in International Application No. PCT/US2017/065516.
(Continued)

*Primary Examiner* — Naomi J Small
(74) *Attorney, Agent, or Firm* — Polsinelli PC

(57) ABSTRACT

Systems and methods of determining physical conditions of a battery, such as state of charge (SOC), state of health (SOH), quality of construction, defect, or failure state include driving two or more acoustic signals of two or more amplitudes, each acoustic signal having two or more frequencies, into the battery and detecting vibrations generated in the battery based on the two or more acoustic signals. Nonlinear response characteristics of the battery for the two or more acoustic signals are determined from the detected vibrations. The physical conditions of the battery are determined based at least in part on the nonlinear response characteristics, using nonlinear acoustic resonance spectroscopy (NARS) or nonlinear resonant ultrasound spectroscopy (NRUS).

22 Claims, 10 Drawing Sheets

(51) Int. Cl.
| | |
|---|---|
| *H01M 10/48* | (2006.01) |
| *G01R 31/389* | (2019.01) |
| *G01R 31/3842* | (2019.01) |
| *G01N 29/12* | (2006.01) |
| *G01N 29/34* | (2006.01) |
| *G01N 29/46* | (2006.01) |
| *B60L 3/00* | (2019.01) |
| *B60L 3/12* | (2006.01) |
| *G01R 31/385* | (2019.01) |
| *B60L 58/16* | (2019.01) |
| *B60L 58/12* | (2019.01) |
| *H01M 10/42* | (2006.01) |
| *G01R 31/367* | (2019.01) |

(52) U.S. Cl.
CPC ............... *B60L 58/12* (2019.02); *B60L 58/16* (2019.02); *G01N 29/12* (2013.01); *G01N 29/346* (2013.01); *G01N 29/348* (2013.01); *G01N 29/46* (2013.01); *G01R 31/385* (2019.01); *G01R 31/389* (2019.01); *G01R 31/3842* (2019.01); *H01M 10/48* (2013.01); *H01M 10/486* (2013.01); *B60L 2240/545* (2013.01); *G01N 2291/025* (2013.01); *G01N 2291/02491* (2013.01); *G01N 2291/2698* (2013.01); *G01R 31/367* (2019.01); *H01M 2010/4271* (2013.01)

(58) Field of Classification Search
USPC .................................................... 340/636.12
See application file for complete search history.

(56) References Cited

U.S. PATENT DOCUMENTS

| | | | |
|---|---|---|---|
| 2010/0310907 A1* | 12/2010 | Miller | H01M 4/485 429/90 |
| 2013/0163768 A1* | 6/2013 | Salter | H04R 29/00 381/56 |
| 2013/0205869 A1* | 8/2013 | Cavaro | G01N 29/036 73/19.03 |
| 2013/0335094 A1* | 12/2013 | Adams | G01R 31/387 324/426 |
| 2016/0139241 A1* | 5/2016 | Holz | H04B 17/318 367/128 |
| 2016/0223498 A1* | 8/2016 | Steingart | G01N 29/4427 |
| 2016/0245875 A1* | 8/2016 | Kircheva | G01R 31/392 |
| 2017/0038344 A1* | 2/2017 | Capus | G01S 15/003 |

OTHER PUBLICATIONS

Liu X et al: "Localization of material defects using nonlinear resonant ultrasound spectroscopy under asymmetric boundary conditions", Physics Procedia, Elsevier, Amsterdam, NL, vol. 3, No. 1, Jan. 1, 2010, pp. 55-61, XP027034311, ISSN: 1875-3892.

Muller Marie et al: "Nonlinear resonant ultrasound spectroscopy (NRUS) applied to damage assessment in bone", The Journal of the Acoustical Society of America, American Institute of Physics for the Acoustical Society of America, New York, NY, US, vol. 118, No. 6, Jan. 1, 2005, pp. 3946-3952, XP012073507, ISSN: 0001-4966, DOI: 10.1121/1.2126917 abstract; figure 4.

* cited by examiner

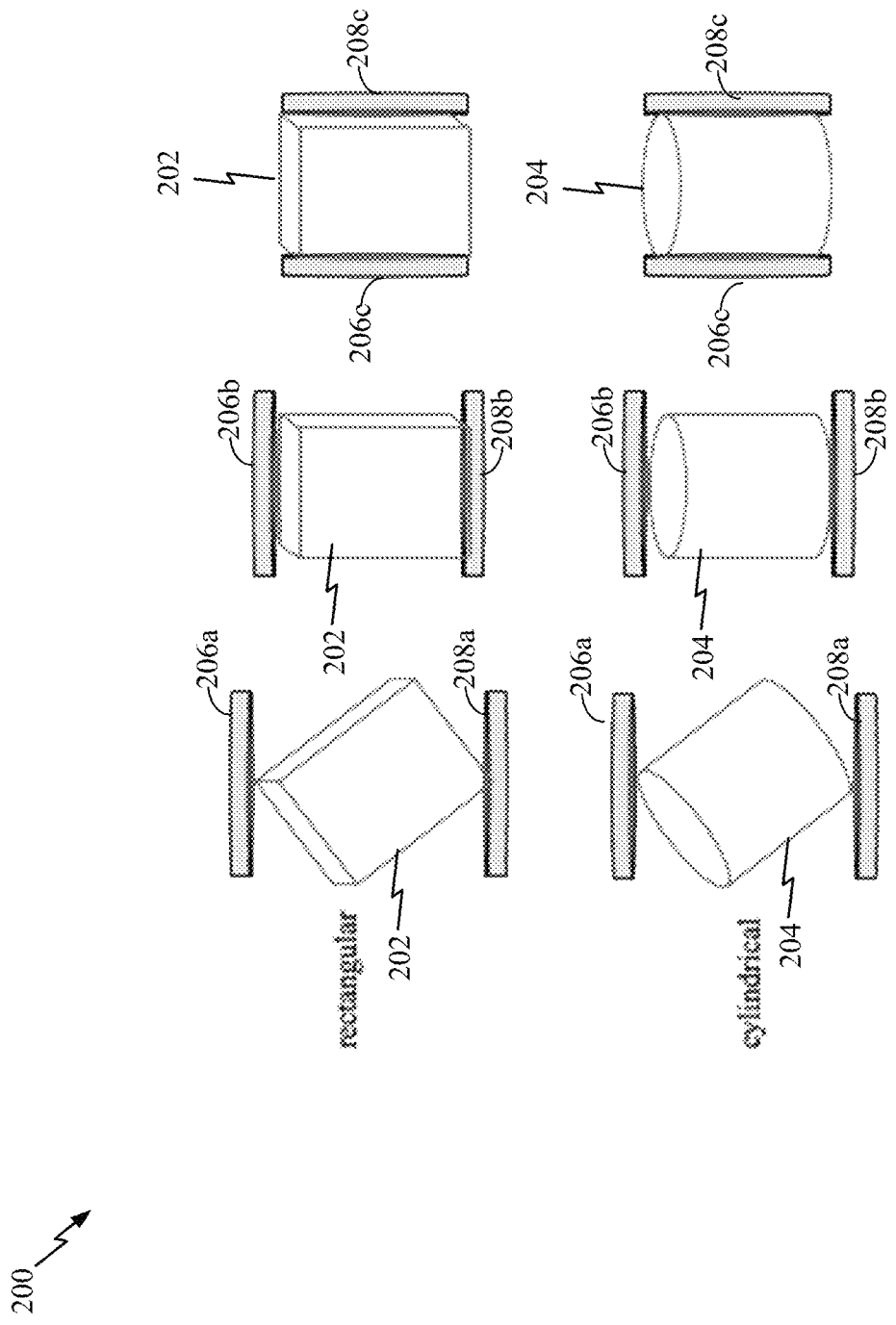

Linear Down-chirp

Logarithmic Down-chirp

Linear Up-chirp

Logarithmic Up-chirp

NONLINEAR ACOUSTIC RESONANCE SPECTROSCOPY (NARS) FOR DETERMINING PHYSICAL CONDITIONS OF BATTERIES

CROSS-REFERENCE TO RELATED APPLICATIONS

The present Application for Patent claims the benefit of Provisional Patent Application No. 62/432,296 entitled "APPARATUS AND METHOD FOR DETERMINING THE PHYSICAL CONDITION OF BATTERIES WITH RESONANT ULTRASOUND SPECTROSCOPY" filed Dec. 9, 2016, and also claims the benefit of Provisional Patent Application No. 62/432,312 entitled "APPARATUS AND METHOD FOR DETERMINING THE PHYSICAL CONDITION OF BATTERIES WITH ACOUSTIC CHIRP SIGNALS" filed Dec. 9, 2016, each of which is assigned to the assignee hereof and hereby expressly incorporated herein by reference in its entirety.

FIELD OF DISCLOSURE

Disclosed aspects are directed to determining physical conditions of batteries. More specifically, exemplary aspects are directed to nonlinear acoustic resonance spectroscopy (NARS) such as nonlinear resonant ultrasound spectroscopy (NRUS) for determining physical conditions of batteries, based on studying nonlinear response characteristics of the batteries to acoustic signals of varying frequencies and amplitudes.

BACKGROUND

The battery industry generally lacks a fast and scalable solution for determining the physical condition of batteries in various stages of their manufacture and use, e.g., during research and development, testing, production, bench assembly, and post fabrication and sealing. The current techniques for diagnosing the physical condition of a battery, e.g., employed at-scale, are limited to electrical and thermal techniques, which are recognized as being inaccurate, destructive, and/or unsuitable for battery diagnostics while the battery is in-use. There is a recognized need for scalable and non-destructive diagnostic techniques for accurately monitoring and assessing a battery's internal state in a way that can inform further analyses of the battery's physical condition, including the ability to determine state of charge (SOC), state of health (SOH), quality of construction, defect or failure state, and other physical properties of the battery.

Current techniques used for battery diagnostics may depend on the specific setting in which the battery is under test. For example, alternating current (AC) impedance spectroscopy and high-precision coulometry may be employed in research settings, although in some cases, other techniques such as high-power synchrotron x-ray diffraction (XRD) and x-ray computed tomography (CT) may also be used. In manufacturing environments, the above-noted research-level techniques may be used along with electrical measurements such as direct current (DC) impedance measurements to gauge internal resistance and initial charge-discharge cycling for gauging capacity, but such techniques may be limited to spot checking. Diagnostic tests performed on every cell of a battery under test may be limited to simple electrical and physical measurements (e.g., open circuit voltage).

With the exception of XRD and CT, the above techniques rely on electrical current being applied to the battery under test, which can be destructive to the battery. However, a drawback of XRD and CT techniques is that they are prohibitively slow and expensive at production scales.

Existing battery diagnostic methods that may be available for detecting or monitoring the physical condition of batteries integrated into electronic devices, electric vehicles, grid-scale energy storage, etc., are typically limited to analyses conducted using electrical tools or thermal sensing. However, these existing diagnostic methods are prone to inaccuracies because they provide averaged data over the entire battery and are not helpful for a more detailed understanding of the internal components, defects, composition distribution, etc., of the battery.

Accordingly, there is emerging research in alternative approaches for determining the physical conditions of batteries which do not rely on electrical tools. In this regard, it is recognized that batteries store energy in the form of chemical potential, wherein during the storage and release of that energy (i.e., during charging and discharging cycles of the battery, respectively), chemical reactions take place that result in a reorganization of mass and a change in materials properties of the battery, including density, modulus, porosity, and thickness. It is also known that the behavior of sound in a material is fundamentally sensitive to these changes in properties. More specifically, the speed of sound through a material is primarily a function of the elastic moduli and density of the material. Moreover, the acoustic impedance of a material (which, like index of refraction for light, influences how sound behaves when entering and leaving a material) is also a strong function of density and moduli. Therefore, it is possible to study and analyze soundwaves passing through the material (or a sample under test) to detect changes in the properties of the material (or sample), which in turn can provide information regarding the physical condition of the material (or sample). Existing approaches for probing a battery using soundwaves are not seen to be sufficiently accurate, nor are they seen to provide a level of detail which would be useful in determining SOH, SOC, possibility of failures, localized defects, etc., whether or not the battery is in use.

Accordingly, there is a recognized need in the industry for detecting a broader scope of physical quality, defects and failure conditions in batteries, either while the battery is deployed and in use or when the battery is not in use.

SUMMARY

Aspects of this disclosure are directed to systems and methods for determining one or more physical conditions of batteries. Exemplary aspects include nonlinear resonant ultrasound spectroscopy (NRUS) or more generally, nonlinear acoustic resonance spectroscopy (NARS) of a battery or sample thereof. In example implementations, two or more acoustic signals of two or more amplitudes, each acoustic signal having two or more frequencies, are driven into the battery, for example by driving transducers which convert electrical signals to vibrations or other means for driving acoustic signals into the battery. The resulting vibrations in the battery from the two or more acoustic signals are detected by receiving transducers or other means for detecting vibrations. Two or more resonance frequencies for the two or more acoustic signals are obtained, for example by studying frequency characteristics (e.g., based on a Fourier transform) of the resulting vibrations. The resonance frequencies of the battery are observed to shift (e.g., following a specific slope or curve) based on the amplitudes of the acoustic signals. Elastic nonlinearities in the battery (e.g., caused by different physical conditions related to state of charge (SoC), state of health (SoH), defects, quality of construction, failure state, etc.) lead to variations in the shift (e.g., slope or curve thereof) in the resonance frequencies. The one or more physical conditions of the battery based at least in part on the nonlinear response characteristics may be determined based on a slope or curve between the two or more resonance frequencies. By studying the shifts in resonance frequencies for two or more batteries or two or more samples of the same battery, information regarding the physical conditions of the batteries may be obtained.

For example, an exemplary aspect is directed to a method of determining one or more physical conditions of a battery, the method comprising driving two or more acoustic signals of two or more amplitudes, each acoustic signal having two or more frequencies, into the battery and detecting vibrations generated in the battery based on the two or more acoustic signals. Nonlinear response characteristics of the battery for the two or more acoustic signals are determined from the detected vibrations. One or more physical conditions of the battery are determined based at least in part on the nonlinear response characteristics.

Another exemplary aspect is directed to an apparatus comprising means for driving two or more acoustic signals of two or more amplitudes, each acoustic signal having two or more frequencies, into a battery and means for detecting vibrations generated in the battery based on the two or more acoustic signals. The apparatus further comprises means for determining nonlinear response characteristics of the battery for the two or more acoustic signals, from the detected vibrations, and means for determining one or more physical conditions of the battery based at least in part on the nonlinear response characteristics.

BRIEF DESCRIPTION OF THE DRAWINGS

The accompanying drawings are presented to aid in the description of various aspects of the invention and are provided solely for illustration and not limitation.

FIGS. 2A-C illustrate examples of various transducer arrangements for probing different bending or excitation modes of batteries using nonlinear acoustic resonance spectroscopy (NARS).

DETAILED DESCRIPTION

Figure 1A:
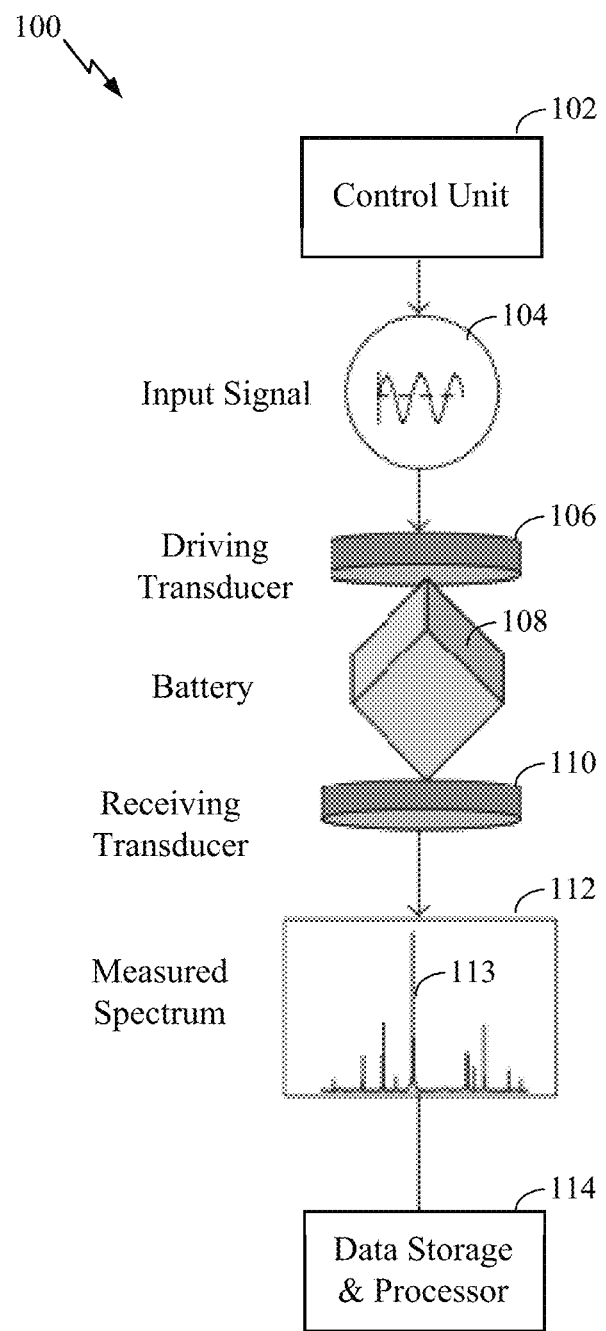
FIGS. 1A-B illustrate views of an example system for nonlinear acoustic resonance spectroscopy (NARS) of batteries.

Aspects of the invention are disclosed in the following description and related drawings directed to specific aspects of the invention. Alternate aspects may be devised without departing from the scope of the invention. Additionally, well-known elements of the invention will not be described in detail or will be omitted so as not to obscure the relevant details of the invention.

The word "exemplary" is used herein to mean "serving as an example, instance, or illustration." Any aspect described herein as "exemplary" is not necessarily to be construed as preferred or advantageous over other aspects. Likewise, the term "aspects of the invention" does not require that all aspects of the invention include the discussed feature, advantage or mode of operation.

The terminology used herein is for the purpose of describing particular aspects only and is not intended to be limiting of aspects of the invention. As used herein, the singular forms "a," "an," and "the" are intended to include the plural forms as well, unless the context clearly indicates otherwise. It will be further understood that the terms "comprises", "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Further, many aspects are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer-readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the aspects described herein, the corresponding form of any such aspects may be described herein as, for example, "logic configured to" perform the described action.

As previously mentioned, there are emerging efforts to exploit the above-described relationships between soundwaves travelling through an object and physical properties of the object, and to use sound and acoustics to gather physical information about the internal components of electrochemical cells and batteries. Specifically, soundwaves may be input into a battery (or more generally, an object or sample under test which may include one or more batteries or portions thereof), and the acoustic or vibrational response may then be measured as the input soundwave travels through the sample. Minor changes or differences in the physical properties of the sample can result in changes to the measured waveforms by these techniques.

To explain, soundwaves propagate through a material in the form of localized pressure change or vibrations. An increase in the localized pressure of the material may lead to a corresponding increase in the local temperature. It is well-known that the speed of sound increases with temperature. Therefore, the local speed of sound increases with an increase in local temperature. If the soundwaves are represented by acoustic signals having different frequencies (e.g., sinusoidal waveforms with different oscillating frequencies) then the different frequencies may have different effects on the material properties of the medium.

By introducing soundwaves of different frequencies into the material, the response characteristics of the material or sample thereof for the different frequencies may be obtained. The response characteristics may reveal information pertaining to harmonics or resonance frequencies which are unique to each sample. Thus, input acoustic signals with broad frequency content may be used to infer a variety of information about the material or sample thereof through which the acoustic signals pass, wherein the information may vary based on attributes such as feature size, layer thickness, porosity, solid fraction, etc., of the sample. These techniques of analyzing materials by studying response characteristics of the materials to different frequencies of excitation are referred to as acoustic resonance spectroscopy (ARS). When the frequencies of the acoustic signals used for probing the materials are in the ultrasonic range, the above techniques are more specifically referred to as resonant ultrasound spectroscopy (RUS). In ARS/RUS, the acoustic signals are modulated to a desired range of frequencies to be used in the diagnosis of materials such as batteries or components thereof.

This information obtained from ARS/RUS of a material or sample thereof is recognized to be different from the acoustic time-of-flight (ToF) measurements which may be obtained by studying only the ToF responses of single, narrow-frequency-bandwidth input acoustic signals through the sample. Specifically, in the case of the materials or samples thereof pertaining to batteries, the components of a battery may be dispersive, e.g., exhibit frequency-dependent moduli, due to a variety of microstructural mechanisms including poro-elastic and visco-elastic effects. Therefore, measurement of frequency-dependent properties of the battery using ARS/RUS obtained by passing acoustic signals of a spectrum or range of frequencies through the battery and determining resonance frequencies of the battery is seen to be useful in the industry.

However, while conventional ARS/RUS of batteries may be performed using input acoustic signals of varying frequency content, these acoustic signals used in the ARS/RUS are typically seen to have uniform amplitudes in the time domain (e.g., the two or more frequencies of acoustic signals used for probing the battery are generated at the same driving voltage, causing uniform characteristics of amplitude, power, strain, etc., for the acoustic signal). It is recognized herein that there are inherent limitations in the straightforward application of the conventional ARS/RUS using acoustic signals of uniform amplitudes in battery diagnosis. To explain, even though techniques such as RUS are well-known and conventionally used in fields such as geophysics and materials science for probing physical properties of objects of interest, the RUS analysis is complicated when the objects being analyzed are batteries with various layers (e.g., electrode layers, separators, electrolytes, etc.) which have high damping coefficients and high inelastic behavior. These different layers of non-homogenous characteristics and thicknesses cause the soundwaves to be unevenly dispersed through the batteries. The conventional ARS/RUS analysis using acoustic signals of uniform amplitudes are not capable of revealing accurate information pertaining to such non-homogenous characteristics or non-linearities in the batteries. Additionally, micro-defects generated during charge/discharge cycles have the potential to increase the degree of acoustic nonlinearity present in the battery.

To address the above limitations in the conventional implementations of ARS/RUS, exemplary aspects disclosed herein include techniques for accurate analysis of even the nonlinear and non-homogenous characteristics of the batteries by using acoustic signals of varying frequency content and also varying amplitudes for probing the batteries. For instance, two or more acoustic signals with two or more amplitudes, each acoustic signal having two or more frequencies, are provided as inputs to the battery or sample under test. Response characteristics based on the resulting vibrations in the battery from the two or more acoustic signals are studied to determine harmonics or resonance frequencies (e.g., by performing a Fourier transform or Fast Fourier Transform (FFT) on the response characteristics). It is recognized that soundwaves of different amplitudes will generate different internal strain fields. Nonlinear (an)elastic properties of the battery will then yield different strain dependent moduli, leading to shifts in the resonance frequencies between response characteristics of acoustic signals having different amplitudes. Studying these shifts, e.g., slopes or curves thereof reveals information pertaining to the nonlinear properties. The above acoustic analysis performed using acoustic signals of varying amplitude is referred to as a nonlinear acoustic resonance spectroscopy (NARS) or more specifically, nonlinear resonant ultrasound spectroscopy (NRUS) when the frequencies of the acoustic signals are in the ultrasonic range.

Accordingly, in exemplary aspects, NARS/NRUS of batteries are disclosed, wherein acoustic resonance-based techniques for nondestructive diagnosis of batteries are used for studying the nonlinear behavior of local changes caused by, for example, internal defects, damages, non-uniform degradations, state of charge, changes in composition, etc., in the batteries. The resonance frequencies of the battery under test may be studied as a function of the level or magnitude or amplitude of excitation caused by acoustic signals because as the excitation levels increase, the elastic nonlinearity of the materials may cause corresponding shifts in the resonance frequencies of the battery. The measured change in nonlinear responses is observed to be more sensitive than the change in linear modulus. As previously mentioned, two or more composite material systems such as batteries may be assembled to yield similar resonance frequency when excited with a broad frequency range input signal at a particular amplitude, but will display different shifts in resonance frequency when excited with the same broadband input frequency at multiple amplitudes due to the nonlinear elastic properties of the composite material systems. Thus, a more accurate and detailed analysis of batteries is enabled by using techniques such as NARS/NRUS.

It will be understood that references to "batteries" in this disclosure do not assume any inherent limitation as to any specific type of battery or component cells thereof but are generally meant to cover any type of electrochemical energy storage device, including, for example, single cell batteries as well as multi-cell assemblies such as cell strings, modules, battery packs, etc.

Figure 1B:
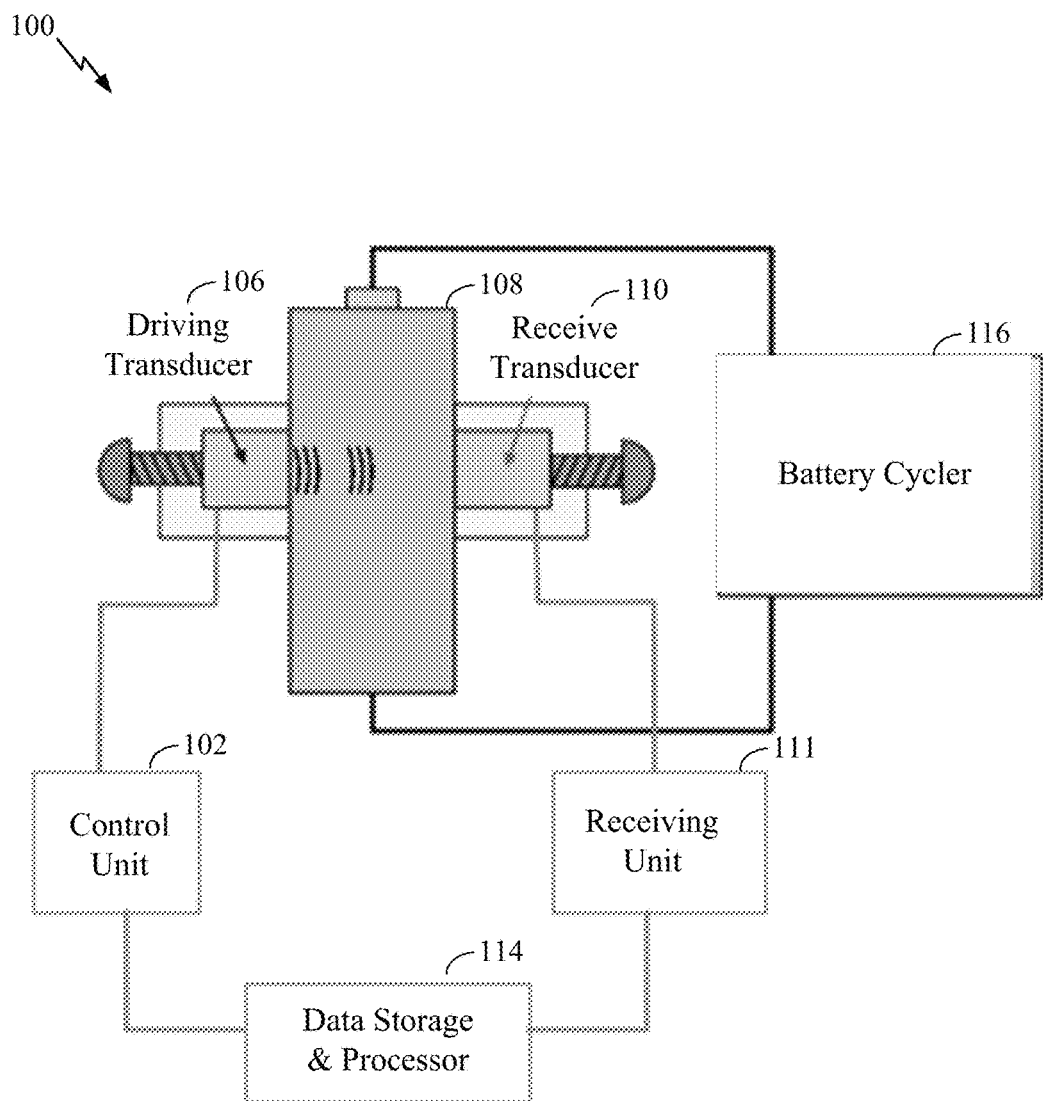

FIGS. 1A-B illustrate different views of exemplary systems which may be configured for performing NARS/NRUS analyses of an object. In general, the exemplary NARS/NRUS analyses may be performed on an object of interest such as battery 108 (which may alternatively be referred to as a battery under test, object under test, sample, etc.) by mechanically exciting or perturbing (i.e., vibrating) battery 108 with input acoustic signals having multiple frequencies (e.g., audible or ultrasound frequencies in the kHz to MHz range) and varying amplitudes. The vibrations generated in battery 108 in response to the mechanical perturbations at the different frequencies may be studied. Means for active actuation such as piezoelectric transducers, vibration motors, shaker tables, etc., may be used in driving perturbations in the form of input acoustic signals of varying amplitudes into battery 108 wherein the input acoustic signals have a range or spectrum of frequencies. Passive actuation of battery 108 can also occur as the result of ambient vibrations in the environment, which, may cause acoustic signals of varying amplitudes and frequencies to be induced in battery 108, and exemplary NARS/NRUS techniques may be extended to studying response characteristics of battery 108 resulting from such passive actuation without deviating from the scope of this disclosure. Regardless of the specific manner in which battery 108 is caused to vibrate, the resulting response vibrations can be detected using piezoelectric transducers, accelerometers, lasers, etc. By collecting and studying the responses to vibrations at various frequencies, the nonlinear response characteristics, and specifically, resonance frequencies may be obtained for different amplitudes. The response characteristics at the different amplitudes may reveal nonlinear mechanical damping or attenuation of the mechanical perturbations at various excitation frequencies at different amplitudes.

In further detail, FIG. 1A shows a schematic view of system 100 configured according to exemplary aspects, while FIG. 1B shows an example implementation of the schematic view of system 100.

Referring to the schematic view of system 100 in FIG. 1A, system 100 is shown to comprise battery 108 whose physical conditions may be diagnosed using exemplary NARS/NRUS analysis. Driving transducer 106 and receiving transducer 110 are separately illustrated as being coupled to battery 108 (couplants may be used to aid in the contact or mechanical coupling of the transducers and respective surfaces of battery 108, but are not required).

Different arrangements or relative placements of driving transducer 106 and receiving transducer 110 with respect to battery 108 are possible and these are explained in more detail with reference to FIGS. 2A-C. The different arrangements can reveal information regarding different bending or excitation modes of battery 108. In the illustration of FIG. 1A, battery 108 is shown as a rectangular cell with driving transducer 106 and receiving transducer 110 placed on opposite edges (e.g., also shown in FIG. 2A). This arrangement shown in FIG. 1A may lead to the most number of excitation modes for the rectangular cell example of battery 108, as acoustic signals traverse the greatest distance through battery 108 between driving transducer 106 and receiving transducer 110 in this arrangement. Other arrangements (e.g., FIGS. 2B-C) may lead to different and/or different numbers of excitation modes of battery 108 and may be utilized in conjunction with or in lieu of the illustrated example arrangement in FIG. 1A. In alternative arrangements, it is also possible to dispose both driving transducer 106 and receiving transducer 110 on the same side of battery 108 or configure the same transducer (or other means for inducing vibrations in a battery and measuring responses to these vibrations) to perform both functions. Measurements of responses on the same side that the vibration was driven may reveal useful information in conjunction with or in lieu of measurements with driving transducer 106 and receiving transducer 110 configured on opposite sides or edges of battery 108.

In an exemplary aspect, input signal 104 may be an acoustic signal having a range of two or more frequencies. Examples of input signal 104 are shown in FIGS. 4A-J and will be explained in more detail in the following sections. Control unit 102 may be configured to generate electrical signals corresponding to the desired input signal 104 (e.g., according to FIGS. 4A-J). In an example implementation, control unit 102 may comprise signal generation means such as an oscilloscope to control the driving voltage of the electrical signal, which would control the amplitude of input signal 104. Control unit 102 may also comprise means for controlling the frequency content of the electrical signal, such as an arbitrary signal generator to generate the frequencies of the electrical signal in the desired range of frequencies for probing battery 108.

Driving transducer 106 may convert the electrical signal represented by input signal 104 to acoustic signals or soundwaves passed through battery 108, which cause mechanical perturbations or response vibrations to be generated in battery 108. In alternative implementations, driving transducer 106 may be replaced or augmented by other means for generating vibrations, such as shaker tables, modal exciters, etc., for transferring soundwaves into battery 108 based on input signal 104. More specifically, example implementations of driving transducer 106 may include any means for driving two or more acoustic signals of two or more amplitudes, each acoustic signal having two or more frequencies, into battery 108.

The vibrational responses generated as a result of the acoustic signals passing through battery 108 may be captured by receiving transducer 110 (which may be alternatively implemented as an accelerometer or laser/optical range-finder to measure the vibrational response of battery 108 caused due to the input signal 104). More specifically, in example implementations, receiving transducer 110 may include any means for detecting vibrations generated in battery 108 based on the two or more acoustic signals driven into battery 108. Receiving transducer 110 may convert the measured response vibrations to electrical signals which may be analyzed for frequency content.

System 100 may further include means for determining nonlinear response characteristics of battery 108 for the two or more acoustic signals, from the detected vibrations. For example, means for performing a Fourier transform or FFT on the signals corresponding to the response vibrations may be provided. Measured spectrum 112 represents a function such as an FFT performed on the frequency content of the response vibrations for a spectrum of frequencies of input signal at a particular amplitude (e.g., measured spectrum 112 as shown may correspond to an FFT of a chirp signal as shown in FIGS. 4D-E, wherein input signal 104 may include two or more chirp signals of two or more amplitudes as shown in the series of linear up-chirp signals in FIG. 4F). For the particular amplitude of an acoustic signal of input signal 104, measured spectrum 112 may reveal resonance frequencies or peaks, of which resonance frequency 113 corresponding to the largest or dominant resonance frequency of battery 108 is particularly identified for example. For different amplitudes of acoustic signals of input signal 104, measured spectrum 112 may vary.

System 100 may also include means for determining one or more physical conditions of the battery based at least in part on the nonlinear response characteristics, e.g., data storage and processor 114. For example, measured spectrum 112 for acoustic signals of various amplitudes of input signal 104, each acoustic signal having varying frequency content, generated from the response vibrations caused by the acoustic signals in battery 108, may be analyzed, stored, etc., in data storage and processor 114. Information derived from the resonance frequencies in measured spectrum 112 for the acoustic signals of different amplitudes is correlated to mechanical properties of battery 108, as will be explained with reference to FIGS. 5A-B in more detail.

As previously mentioned, the response vibrational behavior, and thus resonance frequencies of measured spectrum 112, is seen to depend on the magnitude of the amplitude of input signal 104 (i.e. the magnitude of the strain value of the input vibrations). The resonance frequencies may shift due to nonlinearities (e.g., defects, non-uniformities, etc.) in battery 108, which enables an increased sensitivity in the analysis. Thus, by changing the amplitude of acoustic signals forming input signal 104, the acoustic signals being in a desired frequency range, as in the exemplary NARS/NRUS, information regarding the mechanical properties of battery 108 based on the nonlinear responses may be accurately obtained because even small features in the battery, such as defects in electrodes, particulate contaminants, changes at interfaces, damage to battery components, fractures, etc., can be captured in terms of shifts in resonance frequencies caused at the different amplitudes. In this manner, NARS/NRUS may be used to measure SOC, SOH, physical properties, and physical conditions of batteries.

Furthermore, in some aspects, the charge state of battery 108 may be varied in the course of the NARS/NRUS analyses. The resonance spectrum of battery 108 at a fully charged state (or top of charge) and a fully discharged state (or bottom of charge) may be distinct due to variations in the distributions of modulus and density within battery at each charge/discharge state. Similarly, the resonance spectrum of battery 108 when it is fresh or unused may differ from the resonance spectrum of battery 108 and after it has been subjected to several charge-discharge cycles (also referred to as the battery being cycled), even when the battery is at the same charge state. Accordingly, in exemplary aspects, the resonance spectrum of battery 108 may be obtained in conjunction with a charge cycler for cycling the battery through charge-discharge cycles.

With reference now to FIG. 1B, additional components of system 100 such as battery cycler 116 and receiving unit 111 are also separately illustrated in addition to control unit 102, driving transducer 106, battery 108, receiving transducer 110, and data storage and processor 114 already discussed with reference to the schematic view of system 100 in FIG. 1A. Battery cycler 116 may be connected to leads of battery 108 to cause charge-discharge cycles in battery 108 for the RUS/ARS analysis of battery 108 over the charge-discharge cycles. Receiving unit 111 may perform the functions of receiving the signal outputs from receiving transducer 110 to be used in generating measured spectrum 112 of FIG. 1A, although the functions of receiving unit may be merged into other functional blocks such as data storage and processor 114 without deviating from the scope of this disclosure.

With reference now to FIGS. 2A-C, the previously mentioned example arrangements of transducers with respect to the body of the battery being analyzed using RUS/ARS techniques are discussed in further detail. In general, it is seen that as the distance traveled by acoustic signals through the battery from the driving transducer to the receiving transducer increases, the number of excitation modes or bending modes of the battery materials through which the acoustic signals pass increase. These excitation modes are also different in different directions that acoustic signals traverse the battery. Therefore, the different arrangements as shown in FIGS. 2A-C or the like can reveal information about different cross-sections of the object, and a combination of one or more of these arrangements may be used for obtaining different views or details of the mechanical properties of the object under test.

As shown in FIG. 2A, the two transducers (driving transducer 206a and receiving 206b) are attached to opposing corners of battery 202 (rectangular) or battery 204 (cylindrical). This arrangement in FIG. 2A may enhance the number of excitation modes of respective batteries 202 or 204, respectively.

As in FIGS. 2B, 2C, the respective driving transducers 206b, 206c and receiving transducers 208b, 208c may be attached to opposing sides of battery 202 (rectangular) or battery 204 (cylindrical) in transverse and longitudinal directions. As shown, arrangements in FIG. 2B may lead to more excitation modes than those in FIG. 2C within the respective batteries 202, 204.

In the various arrangements of FIGS. 2A-C, an acoustic gel or elastomeric couplant can be used to improve the mechanical coupling between each transducer (206a-c, 208a-c) and its contact with the battery, to improve the acoustic signal quality. The transducers, using the couplant, may applied to the battery at the desired measurement location. The use of couplant, however, is not required for the exemplary RUS/ARS analyses.

Figure 3:
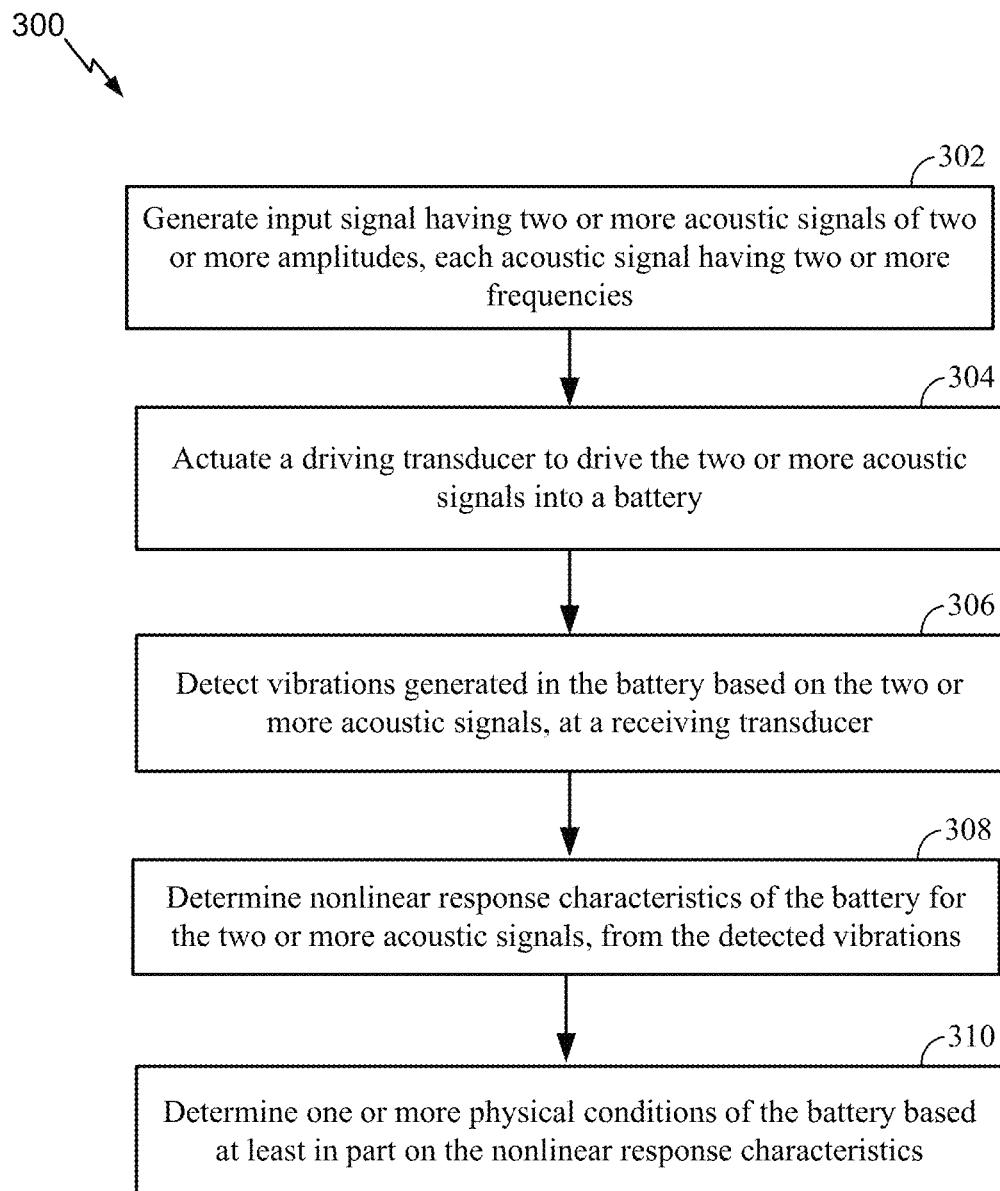
FIG. 3 illustrates a flow-chart of a method of detecting one or more physical conditions of a battery using nonlinear acoustic resonance spectroscopy (NARS), according to aspects of this disclosure.

With reference to FIG. 3, an exemplary process of analyzing physical conditions of a battery under test will be explained. FIG. 3 is a flow-chart of process steps of an exemplary method 300.

Method 300 may start in Block 302, wherein control unit 102, for example, may generate input signal 104 having acoustic signals of varying amplitudes, with each acoustic signal having two or more frequencies, for the exemplary NARS/NRUS of battery 108. Examples of acoustic signal waveforms which may be used as input signal 104 are shown in FIGS. 4A-J.

In Block 304, driving transducer (e.g., transducer 106, 206a-c, etc.) coupled to a battery under test (e.g., battery 108, 202, 204, etc.) may be actuated to drive the two or more acoustic signals of two or more amplitudes, each acoustic signal having two or more frequencies, based on input signal 104, into battery 108, causing nonlinear response vibrations in battery 108 for different amplitudes of the acoustic signals.

In Block 306 receiving transducer (e.g., transducer 108, 208a-c, etc. or an accelerometer) may detect the vibrations generated in battery 108 based on the two or more acoustic signals (e.g., the receiving transducer detects frequency, amplitude, etc., of the response nonlinear vibrations).

Block 308 includes determining nonlinear response characteristics of battery 108 for the two or more acoustic signals, from the detected vibrations. For example, in Block 308, a measured spectrum (e.g., measured spectrum 112) of frequencies of the nonlinear response may be generated as a function (e.g., FFT) of the nonlinear response vibrations detected, wherein the measured spectrum may have one or more resonance frequencies (e.g., resonance frequency 113). It is understood that different amplitudes of acoustic signals in input signal 104 may result in different measured spectrums having different resonance frequencies 113, as will be explained with reference to FIGS. 5A-B.

Block 310 includes determining one or more physical conditions of the battery based at least in part on the nonlinear response characteristics. For example, in Block 310, the resonance frequencies of the measured spectrums corresponding to the different amplitudes of acoustic signals used in input signal 104 may be analyzed to determine one or more physical conditions, such as one or more of a state of charge (SOC), state of health (SOH), quality of construction, defect, or failure state, based on the one or more resonance frequencies. The measured spectrums may be optionally stored in storage medium. Means such as data storage and processor 114 may be configured for the analysis and storage of the measured spectrum.

As noted above, at frequencies near the resonance frequencies of the battery, the response vibrations will be higher in amplitude. Method 300 may be repeated for various arrangements (e.g., as shown in FIGS. 2A-C) of the driving and receiving transducers with respect to the battery under test to obtain one or more measured spectrums which form a complete response vibration profile of the battery. The vibration profile provides a material-dependent and structure-dependent map of the resonance frequencies of the battery under test. In other words, the measured spectrums comprising the resonance frequencies for different amplitudes of acoustic signals used in probing the battery provides a fingerprint which may be unique to the particular physical condition that the battery was in during the measurements, but can be compared to other measurements of batteries of identical construction.

Figure 4A:
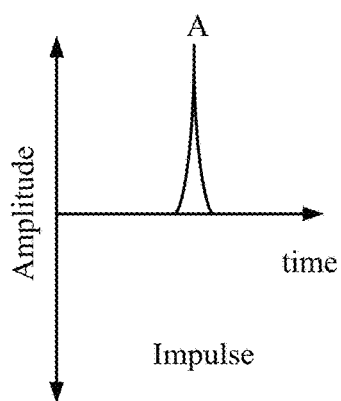
FIGS. 4A-J illustrate waveforms of example acoustic signals that may be used in conducting nonlinear acoustic resonance spectroscopy (NARS) of a battery, according to aspects of this disclosure.
Figure 4B:
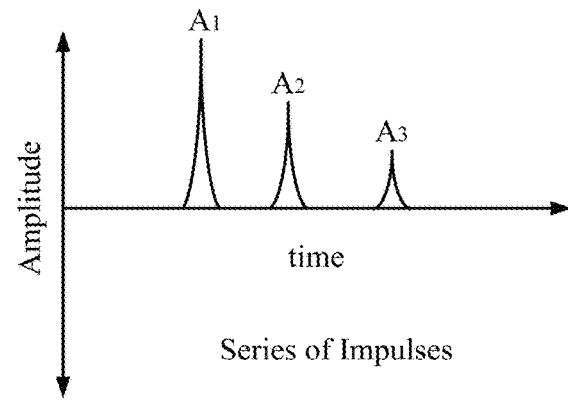
Figure 4C:
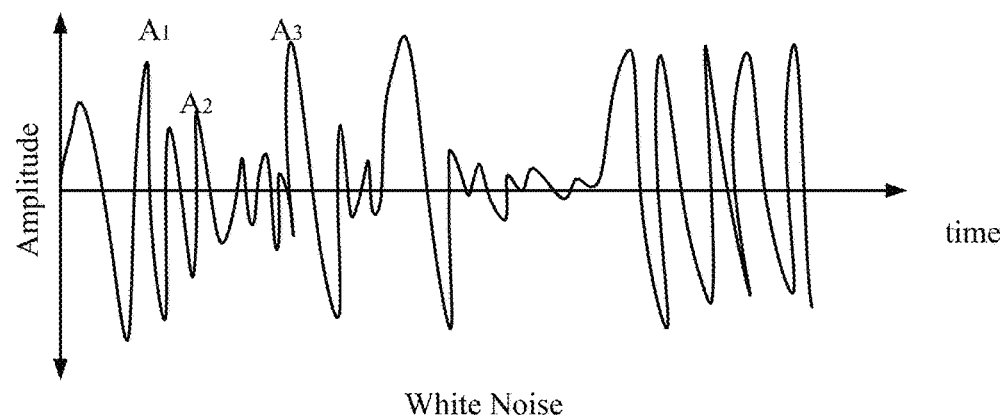
Figure 4E:
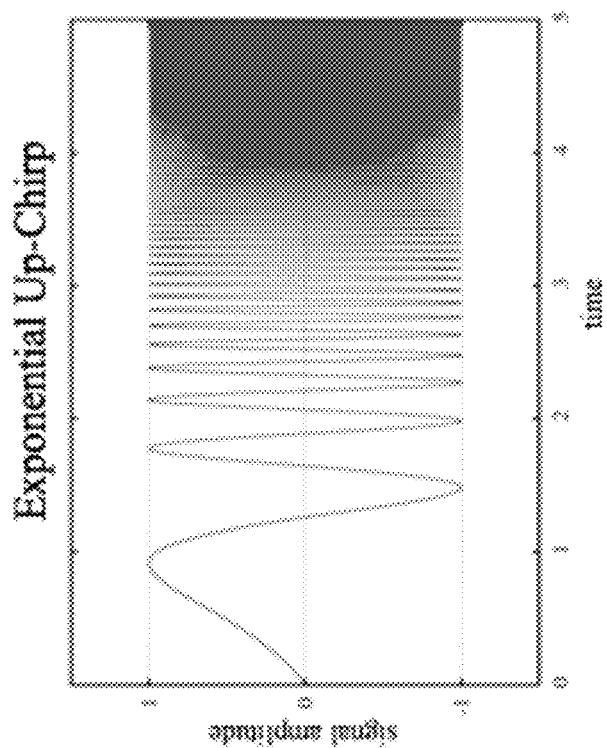
Figure 4D:
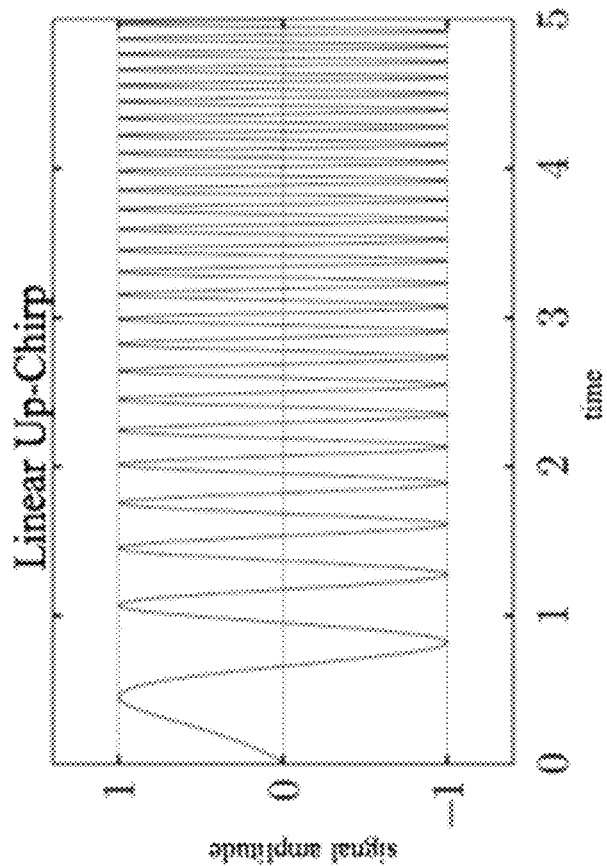

With reference now to FIGS. 4A-J, example waveforms for input signal 104 will be discussed in more detail. FIG. 4A shows an impulse which is a signal of short duration in the time domain and a broad frequency content. Although input signal 104 may be generated as an impulse, as described in the previous sections, sending acoustic signals with a longer dwell time into the battery may allow for easier detection of resonance frequencies (and analysis of corresponding mechanical properties) of the battery. A series of impulses of varying amplitudes $A_1$, $A_2$, $A_3$, etc., as shown in FIG. 4B may be used as two or more acoustic signals of two or more amplitudes which form input signal 104 discussed above, with each acoustic signal having the range of frequencies covered by an impulse signal.

FIG. 4C shows a white noise signal which may have various frequencies and amplitudes. Although a white noise signal may represent two or more acoustic signals of two or more amplitudes, each acoustic signal having two or more frequencies, using a white noise signal as input signal 104 may lead to inefficiencies in NARS/NRUS studies because the amplitudes and frequencies are uncontrolled. Having two or more acoustic signals of different amplitudes but each acoustic signal having the same frequency content may reveal efficient information pertaining to shift in resonance frequencies of nonlinear response vibrations caused by the two or more acoustic signals. Accordingly, the following sections describe acoustic signals having a controlled set of various frequencies which cover a full spectrum of frequencies in a desirable range (e.g., a full spectrum of ultrasonic frequencies), wherein amplitudes of the acoustic signals may be varied to obtain an accurate and complete analysis of the batteries under test.

FIGS. 4D-E illustrate signal waveforms for chirp signals, which are periodic (i.e., sinusoidal) waves with frequencies that vary over time in a controlled manner, e.g., monotonically (i.e., increasing or decreasing). The chirp signals of FIGS. 4D-E have been illustrated to have uniform amplitude, wherein the amplitude may be varied by controlling driving voltage, for example. The frequency change in the chirp signal can happen in either the up (increasing frequency, decreasing wavelength) or down (decreasing frequency, increasing wavelength) direction. This change in frequency change may be linear or nonlinear (e.g., functions such as logarithmic, exponential, etc.). FIG. 4D shows a linear up-chirp signal, which is a chirp signal having monotonically increasing frequencies, the increase being linear. FIG. 4E shows an exponential up-chirp signal, which is a chirp signal having monotonically increasing frequencies, the increase being exponential.

Figure 4F:
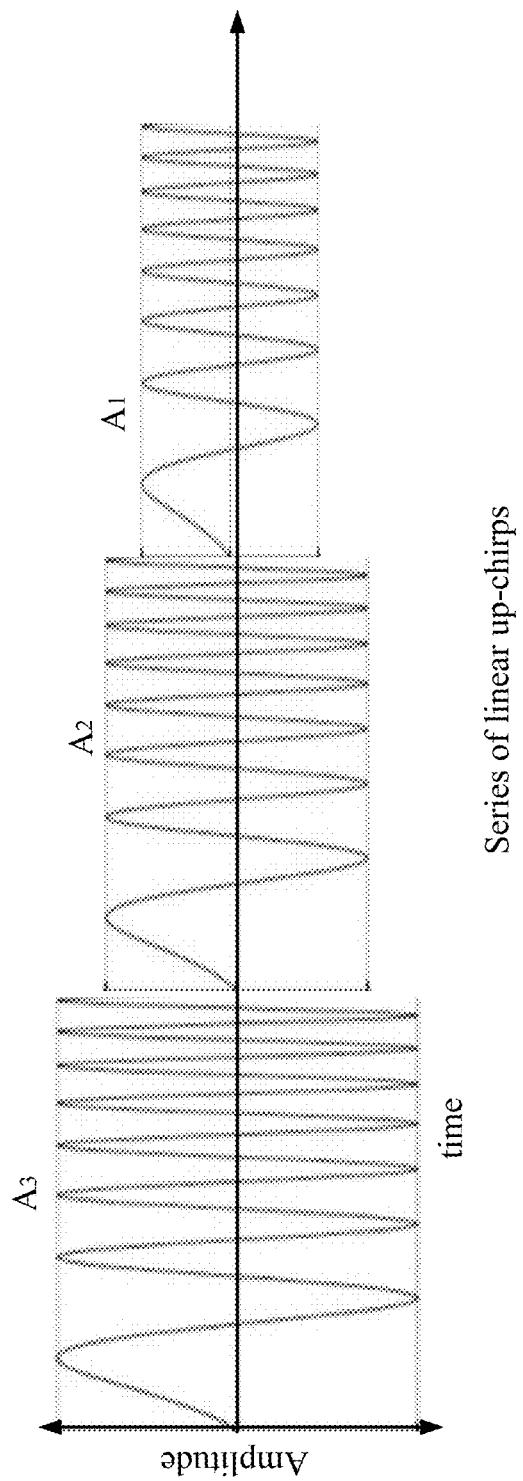

FIG. 4F shows a series of two or more linear up-chirp signals of the type shown in FIG. 4D, with the two or more linear up-chirp signals having different amplitudes $A_1$, $A_2$, $A_3$, etc., but each of the two or more linear up-chirp signals having the same spectrum or range of two or more frequencies. A series of chirp signals of the type shown in FIG. 4F (e.g., series of two or more chirp signals of different amplitudes, each of the two or more chirp signals being up/down linear/logarithmic signals) may be advantageously used as input signal 104 in exemplary NARS/NRUS of battery 108, which will be discussed further in FIGS. 5A-B.

Figure 4H:
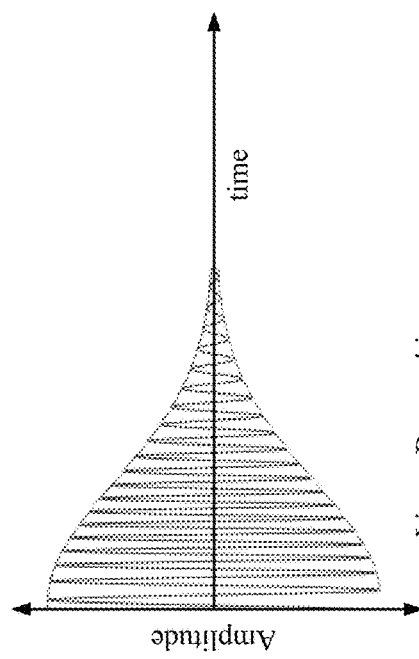
Figure 4J:
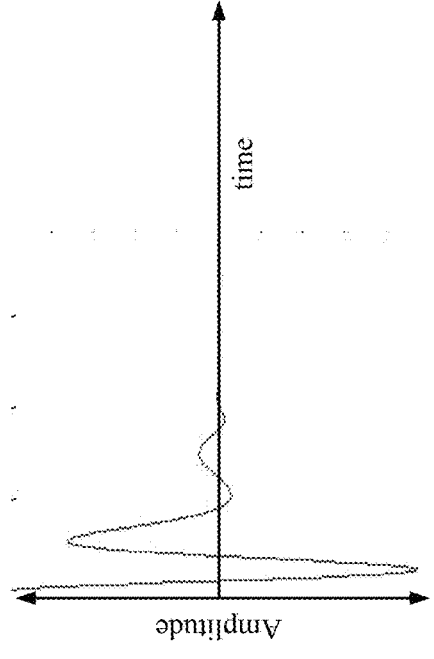
Figure 4G:
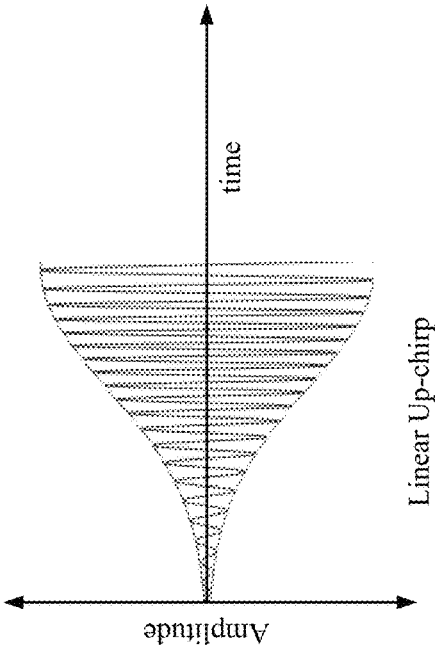
Figure 4I:
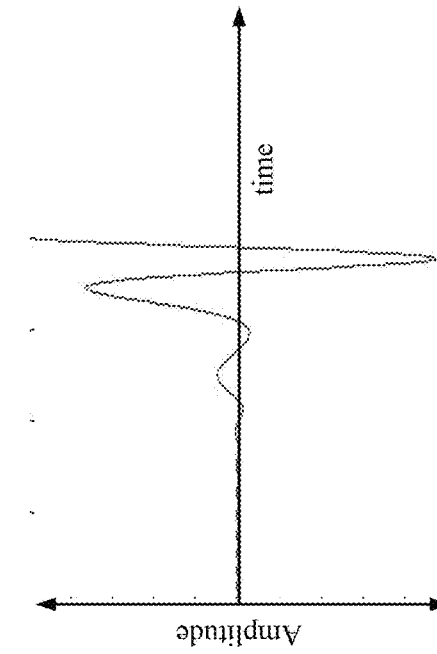

In alternative implementations, chirp signals such as those shown in FIGS. 4G-J having varying amplitudes and covering a range of frequencies may also be used as input signal 104 (although the amplitudes do not need to be varied in any proportion relative to the frequency as the variations in amplitudes and frequencies may be independent). FIG. 4G shows a linear chirp signal having linearly increasing frequencies over time (shown also with linearly increasing amplitudes, without loss of generality); FIG. 4H shows a similar waveform with linearly decreasing frequency over time (with linearly decreasing amplitude), and is referred to as a linear down-chirp; FIG. 4I shows an up-chirp having an exponentially increasing frequencies over time (for increasing amplitudes), and this waveform characteristic is referred to as an exponential up-chirp; and FIG. 4J shows a similar waveform with exponentially decreasing frequency over time or a logarithmic frequency characteristic (with decreasing amplitudes) and is referred to as an exponential down-chirp or logarithmic down-chirp.

While input acoustic signals of a single frequency may be limited by the dispersive nature of the battery components, as discussed above, using chirp signals as shown in FIGS. 4D-J, for example, has been observed to lead to a controlled bandwidth being generated in the input acoustic signal. Accordingly, the dwell time of the input acoustic signals in the frequency domain may be utilized to provide broad-band information even in cases wherein excitation of the battery materials may be inefficient. As can be recognized, using chirp signals may advantageously minimize heat generated during the battery's diagnostics by avoiding the need to repeat input waveforms or measure response vibrations for long periods of time. This is advantageous because a build-up of heat inside the battery over the course of method 300 can skew the measurements or change the materials within the battery being observed or inspected. Moreover, chirps that vary nonlinearly in frequency may also be customized and optimized for particular response characteristics of drivers (e.g., driving transducer 106) and receivers (e.g., receiving transducer 110) of the chirp signals. The input frequencies of acoustic chirps can be in audible (Hz-kHz) and ultrasonic (kHz and above) ranges without loss of generality.

Figure 5A:
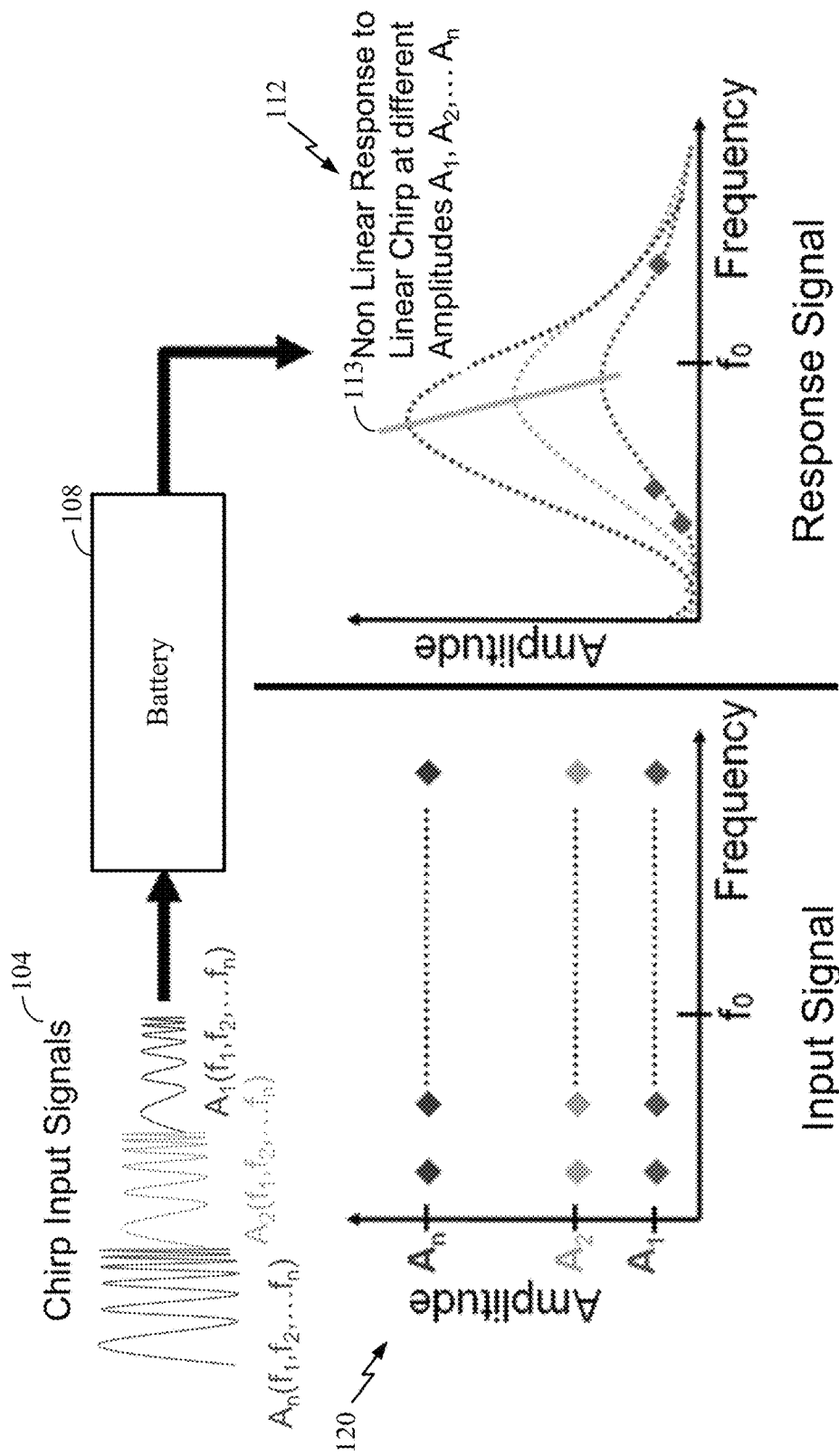
FIGS. 5A-B illustrate exemplary results of conducting nonlinear acoustic resonance spectroscopy (NARS) of one or more batteries, according to aspects of this disclosure.
Figure 5B:
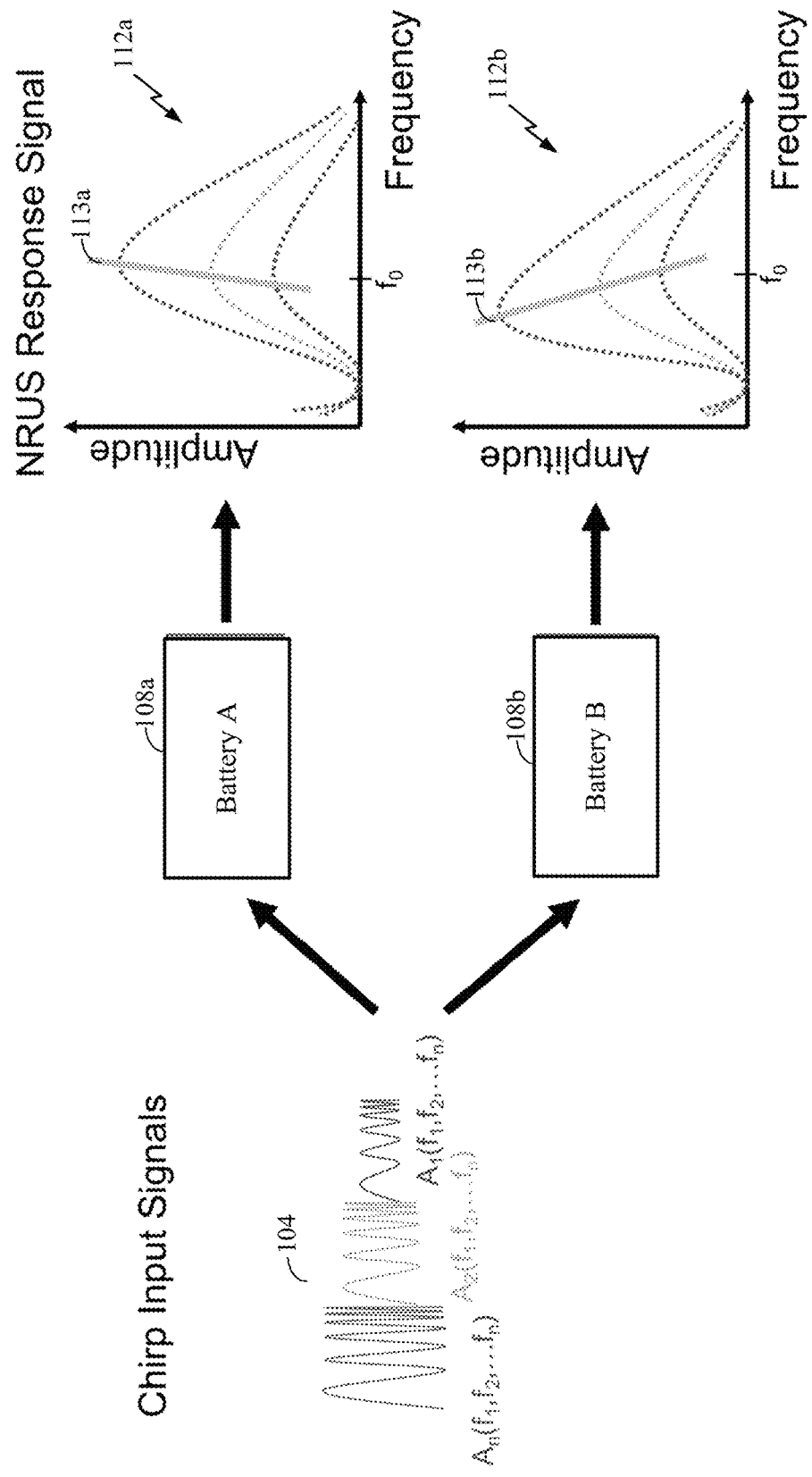

With reference now to FIGS. 5A-B exemplary studies of batteries using NARS/NRUS techniques will be discussed. Starting with FIG. 5A, input signal 104 is shown to comprise a series of chirp signals such as the series of two or more linear up-chirp signals shown in FIG. 4F and discussed above. The two or more chirp signals have two or more corresponding amplitudes $A_1$, $A_2$, . . . , $A_n$, but the same range of frequencies, representatively shown as $f_1$, $f_2$, . . . $f_n$. Plot 120 shows the amplitudes of the chirp signals of input signal 104 as a function of frequencies. Plot 120 shows that for each of the series of chirp signals, the amplitude remains the same across the different frequencies.

Input signal 104 is shown to be provided to battery 108 with the resulting vibrational response shown as measured spectrum 112 (with the various other details of an exemplary setup for this measurement shown in FIGS. 1A-B having been omitted in FIG. 5A for the sake of clarity). As observed from measured spectrum 112, amplitudes of the response vibrations caused in battery 108 vary based on amplitudes and frequencies of the input signal. More specifically, resonance frequency 113 is seen to be different for different amplitudes of the input chirp signals. The resonance frequency 113 for amplitude $A_1$ is shown as occurring at frequency $f_0$, but shifts to the left of this frequency $f_0$ for chirp signals having larger amplitudes $A_2, \ldots, A_n$ for this example (keeping in mind that the shift in resonance frequencies is merely for illustrative purposes without assuming any inherent requirements or limitations in the nature of the shift). The shift in resonance frequencies may be a function of nonlinearities in battery 108. By studying the shifts in various resonance frequencies, information pertaining to the nonlinearities may be obtained.

For example, as shown in FIG. 5B, input signal 104 of FIG. 5A discussed above may be used to probe two batteries, battery A 108a and battery B 108b. In various implementations, battery A 108a and battery B 108b may be different batteries, with battery A 108a having known or baseline properties and battery B 108b being an unknown battery whose physical conditions are being analyzed with respect to battery A 108a; or battery A 108a and battery B 108b may be different versions or samples of the same battery studied at different times or at different states of charge, for example.

Without loss of generality, NRUS response signals for battery A 108a and battery B 108b are shown as measured spectrums 112a and 112b, respectively. Measured spectrums 112a and 112b are shown to have different shifts in respective resonance frequencies 113a and 113b. Comparing these different shifts (e.g., slopes or curves) provides information pertaining to respective or relative physical conditions of battery A 108a and battery B 108b. For example, measured spectrums 112a and 112b analyses of frequency-dependent acoustic data may be reveal information about the physical condition of internal components (e.g., electrode porosity and tortuosity, separator membrane permeability, electrolyte viscosity, visco-elasticity etc.) of battery A 108a and battery B 108b.

For each battery 108, using system 100 with battery cycler 116 as shown in FIG. 1B, the setup shown in FIG. 5A with input signal 104 being a series of two or more chirp signals can provide a corresponding "fingerprint" in the form of measured spectrum 112 at a known state of charge. These fingerprints may be used to compare batteries or determine information pertaining to physical conditions of a battery according to exemplary aspects discussed above.

In exemplary aspects, the input chirp signals may be optimized by varying dwell time in the frequency domain, based on received signal frequency characteristics, thus providing an approach to tune the measurement approach. In some aspects, time-varying filters may also be utilized to assist in suppressing background noise. In some aspects, cross-correlation methods may be used to estimate frequency-dependent arrival times of the transmitted chirp signals. Repeating the above measurement and analysis for multiple driving voltages (i.e., input power, amplitude, or strain) as in the exemplary NARS/NRUS analyses provides useful information regarding the strain-dependent response of the battery under test. As described in foregoing sections, the vibrational response of the battery under test having a nonlinear relationship to the driving voltages (i.e., input power, amplitude, or strain) of the input signal can provide information about the physical condition of the battery with greater accuracy than is possible using conventional ARS/RUS analyses.

In exemplary aspects, an inverse spectrum analysis may also be performed on the response to chirp signals or other input signals with a range of frequency content, based on identified resonance frequencies in the measured spectrum for input signals of varying frequencies and amplitudes. For instance, resonance modes identified using quantitative fitting algorithms may be applied to the measured spectrum 112, for example, which comprises resonance curves for a series of chirp signals as shown in FIGS. 5A-B. Thus, using an inverse spectrum analysis, a computer model of the battery which generated the measured spectrum may be created, based for example, on prior knowledge of some properties of the battery (e.g., geometry, initial chemical makeup, structure and properties of internal components, location of inert and reactive materials within the battery, etc.). The computer model can be used to produce a simulated resonance spectrum (e.g., similar to measured spectrum 112 created using the physical battery). The simulated resonance spectrum can then be compared to the measured spectrum, to detect differences between the simulated and measured spectrums. The parameters in the computer model can be updated to account for the differences and to include any potential or likely changes in the battery, and the simulation can be rerun and comparison remade in an iterative fashion. Once the difference between the simulated and measured resonance spectrums is sufficiently small (e.g., smaller than a pre-determined threshold), the computer model may be considered to accurately represent the true physical condition of the battery.

In exemplary aspects, updates to the parameters of the computer model can be informed by knowledge of the properties of the battery and the principles of electrochemistry. For example, in a lithium ion battery model, the parameters can include distribution of lithium ions in the structure of the graphite electrode during charging or discharging, and gas generation per cycle based on existing knowledge of that battery.

The exemplary NARS/NRUS based battery diagnostic techniques may be advantageously applied in research and development of battery materials, quality control at various stages during battery manufacturing, post-assembly quality control, and inspection of quality and expected performance in recently-purchased batteries (e.g., by a battery integrator).

Another example application is in the emerging second-life market to inspect and assess retired batteries (e.g., electric vehicle batteries) to determine the remaining lifetime and usability in secondary applications (e.g., in grid-related applications) or recyclability. Yet another example application for the exemplary technology is monitoring of battery SOC and SOH while in operation, as the batteries are used in consumer electronic devices, electric vehicles, grid-scale energy storage systems, etc.

Further, those of skill in the art will appreciate that the various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The methods, sequences and/or algorithms described in connection with the aspects disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium.

Accordingly, an aspect of the invention can include a computer-readable media embodying a method for determining one or more physical conditions of a battery using acoustic signals, including chirp signals. Accordingly, the invention is not limited to illustrated examples and any means for performing the functionality described herein are included in aspects of the invention.

While the foregoing disclosure shows illustrative aspects of the invention, it should be noted that various changes and modifications could be made herein without departing from the scope of the invention as defined by the appended claims. The functions, steps and/or actions of the method claims in accordance with the aspects of the invention described herein need not be performed in any particular order. Furthermore, although elements of the invention may be described or claimed in the singular, the plural is contemplated unless limitation to the singular is explicitly stated.

What is claimed is:

1. A method of determining one or more physical conditions of a battery, the method comprising:
    driving two or more acoustic signals of two or more amplitudes, each acoustic signal having two or more frequencies, into the battery, wherein the two or more acoustic signals comprise corresponding two or more chirp signals, the two or more frequencies being the same and in the same frequency range for all of the two or more chirp signals;
    detecting vibrations generated in the battery based on the two or more acoustic signals;
    determining nonlinear response characteristics of the battery for the two or more acoustic signals, from the detected vibrations, wherein the nonlinear response characteristics of the battery for the two or more acoustic signals comprise two or more resonance frequencies corresponding to the two or more amplitudes of the two or more acoustic signals;
    determining a slope or curve between the two or more resonance frequencies;
    comparing the nonlinear response characteristics of the battery to a reference nonlinear response characteristics, based on comparing the slope or curve to a reference slope or curve; and
    determining one or more physical conditions of the battery based at least in part on comparing the nonlinear response characteristics.

2. The method of claim 1, wherein the one or more physical conditions comprise one or more of a state of charge (SOC), state of health (SOH), quality of construction, defect, or failure state.

3. The method of claim 1 comprising a nonlinear acoustic resonance spectroscopy (NARS) or nonlinear resonant ultrasound spectroscopy (NRUS) of the battery.

4. The method of claim 1 comprising generating the two or more acoustic signals based on two or more driving voltages, wherein the two or more amplitudes of the two or more acoustic signals cause two or more strain values applied to the battery.

5. The method of claim 1, wherein each of the two or more chirp signals is one of: an up-chirp two or more frequencies comprising monotonically increasing frequencies; or a down-chirp with two or more frequencies comprising monotonically decreasing frequencies.

6. The method of claim 1, wherein each of the two or more chirp signals is one of: a linear chirp with two or more frequencies comprising linearly varying frequencies; or a nonlinear chirp with two or more frequencies comprising a nonlinear function of frequencies, the nonlinear function comprising an exponential, logarithmic function.

7. The method of claim 1, further comprising varying a state of charge of the battery between a fully charged state and a fully discharged state.

8. The method of claim 1, comprising driving the acoustic signal by a driving transducer coupled to the battery and detecting the vibrations in a receiving transducer or accelerometer coupled to the battery.

9. The method of claim 8, comprising placing the driving transducer and the receiving transducer with respect to the battery based on desired excitation modes, wherein the placing includes disposing the driving transducer and the receiving transducer on opposite sides or edges of the battery.

10. The method of claim 9, wherein the placing includes disposing the driving transducer and the receiving transducer on the same side of the battery.

11. The method of claim 1, wherein the reference nonlinear response characteristics comprise nonlinear response characteristics of a reference battery based on vibrations caused by driving the two or more acoustic signals into the reference battery.

12. The method of claim 11, wherein the battery and the reference battery are different batteries.

13. The method of claim 12, wherein a state of charge (SOC) or voltage of the battery is different from a corresponding SOC or voltage of the reference battery.

14. The method of claim 12, wherein a state of charge (SOC) or voltage of the battery is equal to a corresponding SOC or voltage of the reference battery.

15. The method of claim 11, wherein the battery and the reference battery are the same battery, and wherein the battery and the reference battery have different states of health (SOHs).

16. The method of claim 15, wherein a state of charge (SOC) or voltage of the battery is different from a corresponding SOC or voltage of the reference battery.

17. The method of claim 15, wherein a state of charge (SOC) or voltage of the battery is equal to a corresponding SOC or voltage of the reference battery.

18. An apparatus comprising:
    means for driving two or more acoustic signals of two or more amplitudes, each acoustic signal having two or more frequencies, into a battery, wherein the two or more acoustic signals comprise corresponding two or more chirp signals, the two or more frequencies being the same and in the same range for all of the two or more chirp signals;
    means for detecting vibrations generated in the battery based on the two or more acoustic signals;
    means for determining nonlinear response characteristics of the battery for the two or more acoustic signals, from the detected vibrations, wherein the nonlinear response characteristics of the battery for the two or more acoustic signals comprise two or more resonance frequencies corresponding to the two or more amplitudes of the two or more acoustic signals;

determining a slope or curve between the two or more resonance frequencies;

means for comparing the nonlinear response characteristics of the battery to a reference nonlinear response characteristics, based on comparing the slope or curve to a reference slope or curve; and means for determining one or more physical conditions of the battery based at least in part on comparing the nonlinear response characteristics.

19. The apparatus of claim 18, wherein the one or more physical conditions comprise one or more of a state of charge (SOC), state of health (SOH), quality of construction, defect, or failure state.

20. The apparatus of claim 18, comprising means for generating the two or more acoustic signals based on two or more driving voltages, wherein the two or more amplitudes of the two or more acoustic signals cause two or more strain values applied to the battery.

21. The apparatus of claim 18, further comprising means for varying a state of charge of the battery between a fully charged state and a fully discharged state.

22. The apparatus of claim 18, wherein the means for driving the two or more acoustic signals and the means for detecting the vibrations are disposed on opposite sides or edges of the battery or on the same side of the battery.

* * * * *

UNITED STATES PATENT AND TRADEMARK OFFICE
CERTIFICATE OF CORRECTION

PATENT NO. : 10,502,793 B2
APPLICATION NO. : 15/836531
DATED : December 10, 2019
INVENTOR(S) : Hsieh et al.

Page 1 of 1

It is certified that error appears in the above-identified patent and that said Letters Patent is hereby corrected as shown below:

In the Specification

In Column 1, Line 22, before the "FIELD OF DISCLOSURE", please insert the following paragraph:
--Statement Regarding Federally Sponsored Research or Development
This invention was made with U.S. Federal Government support under Contract No. DE-AC02-05CH11231 awarded by the U.S. Department of Energy and under Grant No. SBIR 1621926 awarded by the National Science Foundation. The U.S. Federal Government has certain rights in the invention.--

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*